United States Patent
Wang et al.

(10) Patent No.: US 6,752,938 B2
(45) Date of Patent: Jun. 22, 2004

(54) METHOD OF PREPARING MICROSPHERE COMPOSITE OF COLLAGEN AND BIOCERAMIC POWDER

(75) Inventors: Yng-Jiin Wang, Taipei (TW); Shiao-Wen Tsai, Taipei (TW); Hsiu-Hsuan Huang, Taipei (TW); Wen Chung Chang, Taipei (TW)

(73) Assignee: Invigor Biotechnology Co., Ltd., Taipei (TW)

( * ) Notice: Subject to any disclaimer, the term of this patent is extended or adjusted under 35 U.S.C. 154(b) by 404 days.

(21) Appl. No.: 09/977,591

(22) Filed: Oct. 13, 2001

(65) Prior Publication Data

US 2003/0071380 A1 Apr. 17, 2003

(51) Int. Cl.[7] ................................. B29B 9/00
(52) U.S. Cl. .......................... 264/5; 264/7; 424/423; 424/426; 424/499; 514/2
(58) Field of Search .................. 264/5, 7; 424/423, 424/426, 499; 514/2

(56) References Cited

U.S. PATENT DOCUMENTS

| | | | |
|---|---|---|---|
| 4,776,890 A | 10/1988 | Chu | 106/151.1 |
| 4,888,366 A | 12/1989 | Chu et al. | 523/115 |
| 6,485,751 B1 * | 11/2002 | Wang | 424/499 |
| 2001/0044412 A1 * | 11/2001 | Wolff et al. | 514/44 |

FOREIGN PATENT DOCUMENTS

TW 420604 2/2001 ............ A61F/2/02

* cited by examiner

Primary Examiner—Mary Lynn Theisen

(57) ABSTRACT

This invention provides a method of preparing microsphere composite of collagen and bioceramic powder. This method first mixes a collagen solution with bioceramic powder and alginate, and squeezes the mixture solution to spherical droplets being discharged into a divalent cation solution undergoing gelling to form microspheres. Next, the microsphere is coated with a chitosan solution. Then, interior alginate and surface chitosan of the microsphere are liquefied and washed out with an aqueous buffer solution such as phosphate based buffer, and collagen in the microsphere is reconstituted to fiber network at the same time. The prepared microsphere composite has similar composition components of bone tissue, and the collagen thereof has a network of reconstituted fibers. The microsphere composite of this invention provides a similar growth environment of bone tissue cells, is used as a carrier to carry cells, coat and fix bone growth factors, and is applied in bone repair.

18 Claims, 5 Drawing Sheets

```
┌─────────────────────────────────────────────────────────────┐
│ Mix a collagen solution with bioceramic powder and alginate │
└─────────────────────────────────────────────────────────────┘
                    ⇩  ┌──────────────────────────────────────┐
                       │ Spherical droplets are discharged at 4°C │
                       └──────────────────────────────────────┘
                    ⇩
            ┌──────────────────────────────┐
            │ Divalent cation solution, 4°C │
            └──────────────────────────────┘
                    ⇩
                ┌──────────────────┐
                │ Ca-CHES wash, 4°C │
                └──────────────────┘
                    ⇩
        ┌────────────────────────────────────────┐
        │ Coating of chitosan solution, room temperature │
        └────────────────────────────────────────┘
                    ⇩
    ┌────────────────────────────────────────────────────┐
    │ Liquefying and washing out alginate and chitosan, 37°C │
    └────────────────────────────────────────────────────┘
                    ⇩
                ┌────────────────────┐
                │ Phosphate buffer wash │
                └────────────────────┘
                    ⇩
┌─────────────────────────────────────────────────────────────┐
│ Microsphere composite is freeze-dried and preserved at -20°C │
│ or preserved in phosphate buffer saline at 4°C              │
└─────────────────────────────────────────────────────────────┘
```

FIG. 1

METHOD OF PREPARING MICROSPHERE COMPOSITE OF COLLAGEN AND BIOCERAMIC POWDER

FIELD OF THE INVENTION

This invention relates to a method of preparing microsphere composite and in particular to a method of preparing microsphere composite of collagen and bioceramic powder, the interior and the surface of the microsphere have a three dimensional network of collagen fibers.

BACKGROUND OF THE INVENTION

Human bone tissue needs to be repaired as it has defects due to damages or diseases. If bone implant material is added to the defect to bear stress and provide a scaffold for cell culturing, which can effectively augment bone structures and induce bone tissue regeneration and repair. The best method to get bone implant material is autogenous implant, but this source is limited and the patient suffers a second operation. Allogenous bone graft has problems of immune response and other side effects. Therefore, the synthetic bone tissue material gives another choice. The conventional synthetic implant material has inertia in order to coexist with living tissues. But the inertia material induces fibers around the implant, therefore the implant is not fixed or the tissues around it become fibers or die. Prior arts have discovered there is biological binding between tissue and biomaterial, and the biomaterial has better biocompatibility. Collagen is the most abundant protein of bone matrix, has biocompatibility and low immune response causing property, and provides a suitable matrix for regenerated osteocyte's anchorage. Adding bioceramic powder such as tricalciun phosphate (TCP), hydroxyapatite (HAP) to collagen forms composite material, this composite material has larger mechanical strength and further simulates the composition components of bone tissue. Such composite material can be used as carriers for cells and growth factors which induce tissue regeneration and speed up bone repair rate.

There are many shapes of implant materials such as bulk shape, cement shape, and microsphere shape. Each shape has its own disadvantages. Bulk shape bone implant has larger mechanical strength, so it is not suitably applied in various shapes of bone defect in operation. As per cement shape and microsphere shape bone implants, which can be conveniently operated, molded in accordance with the shape of the defect, and injected to the location of bone defect to reduce patient's pain in the operation. The disadvantages of materials of these shapes are such materials can not be easily fixed at the defect and have smaller mechanical strength.

Conventional technology filled collagen in the pores of sintered porous ceramic materials via pouring or immersion. Sintered ceramics has high hardness to bear stress, but has limitation in modability. In addition, the porous ceramic is not bioresorbable and an obstacle to further growth of new bone tissues.

Prior art mixed the hydroxyapatite dissolved in acidic solution with reconstituted collagen, then adjusted the pH of the solution to slightly basic to make hydroxyapatite dispersed in collagen. Prior art also mixed hydroxyapatite precursor with collagen solution, and used acid-base reaction to convert the precursor to hydroxyapatite dispersed in collagen fibers matrix. Chu et al in 1988, 1989 (U.S. Pat. Nos. 4,776,890, 4,888,366), mixed collagen solution with hydroxyapatite powder directly to form gel solution, which has injectable advantages and applications to repair of soft tissues. The above composite material formed by direct mixing of the composition components is separated into two phases after a period of time due to appreciable specificity difference between collagen and bioceramic powder. In addition, the diameter of bioceramic powder used is about 0.5 mm which is too large, this type of bioceramic is not bioresorbable and induces fiber tissues around it. This direct mixed composite can not form similar collagen fibrous network of bone tissues providing the needed growth environment of bone tissue cells via an observation of the microscopic structure of the composite.

In microsphere composite material, collagen and bioceramic powder are distributed more homogeneously. Large amount of the microspheres can be arranged in any orientation, and this remedies nonhomogeneity of two phases of each microsphere macroscopically. In addition, the microsphere has good modability and can be prepared in injectable form to reduce the need of operation due to its small diameter. Prior art used silicon oil to prepare microsphere of collagen, then further mixed hydroxyapatite with collagen solution, the mixture was discharged into a fast agitated ethyl-2-hexyl cocoate to make collagen form sphere, the solution was centrifuged and ethyl alcohol was added to the solution to remove ethyl-2-hexyl cocoate to separate microsphere of collagen and hydroxyapatite. Wang et al in 2001 (ROC Patent Publication No. 420604) mixed collagen solution with hydroxyapatite to form a mixture solution, spherical droplets of which were discharged into an oil phase such as olive oil, the collagen of the mixture solution reconstituted to form fiber network microsphere, a cross-linking agent such as glutaraldehyde was added to the oil phase to make the reconstituted collagen link with the hydroxyapatite, finally the microsphere was separated from the oil phase. In the above process to prepare microsphere, organic solvent used might damage collagen structure, and it is worried about that residual organic oil or cross-linking agent in the prepared microsphere causes damages to tissues. In addition, more processes are needed to separate the oil phase.

SUMMARY OF THE INVENTION

The object of the present invention is to provide a method of preparing microsphere composite of collagen and bioceramic powder in order to improve the drawbacks of conventional methods to prepare composite material. The present invention uses collagen solution and reconstitution technology to prepare the microsphere composite. Collagen and bioceramic powder are distributed homogeneously in the microsphere composite, and the interior and the surface of the microsphere have a three dimensional network of collagen fibers. There is no residual organic solvent, organic oil or cross-linking agent in the prepared microsphere composite, so there is no need to worry about they may cause damages to tissues. In addition, the microsphere composite of this invention has enough mechanical strength to be used as a carrier to carry cells, coat and fix different bone growth factors to induce tissue regeneration and speed up bone repair rate. The microsphere composite can be injected in bone repair or further processed to different shapes of plate to be applied in bone repair.

BRIEF DESCRIPTION OF THE DRAWINGS

FIG. 1 is a diagram showing the steps of preparing microsphere composite of collagen and bioceramic powder in accordance with Example 1.

DETAILED DESCRIPTION OF PREFERRED EMBODIMENTS

Figure 2A:
FIG. 2A shows a scanning electron microscopy (SEM) micrograph of the cross section of the microsphere composite after the 9 hours wash (Example 1), and the magnification is 10000×.

The method of this invention prepares microsphere composite of collagen and bioceramic powder as follows: Mix a collagen solution with bioceramic powder and alginate at about 0–10° C., then the mixture solution is squeezed to spherical droplets being discharged into a divalent cation solution undergoing gelling to produce microspheres. The microsphere is coated with a chitosan solution to support the shape of the microsphere and provide the microsphere with enough mechanical strength to maintain its structure such that the microsphere can be used as a carrier. Interior alginate and surface chitosan of the microsphere are liquefied and washed out with an aqueous buffer solution such as phosphate based buffer, while collagen in the microsphere is reconstituted to fiber network at the same time at about 35–40° C. Such washed microsphere composite of collagen and bioceramic powder is further freeze-dried and preserved at about −20° C. or directly preserved in phosphate buffer saline at about 4° C.

The collagen used in this invention can be any type of collagen. The embodiments of this invention use purified atelopeptides of type I and type II animal collagens to demonstrate the present invention. Enzyme such as pepsin is applied to collagen to remove the terminal telopeptides causing immune response, thus formation of collagen fiber by aggregation of collagen does not occur and formation of collagen solution occurs. The collagen solution can be reconstituted to collagen fiber network under some specific conditions. Because telopeptides are removed, the immunogenic property of the collagen is reduced appreciably. The microsphere composite of this invention comprises about 1–99% of collagen by weight with respect to the total weight of the microsphere, and the concentration of collagen solution is prepared as about 0.1–20 mg/ml for use in the embodiment.

The most abundant component of bone tissue matrix is mineral, which is mainly bioapatite of low crystallinity formed by calcium phosphate and calcium carbonate. The bioceramic powder (particle) used in this invention is selected from the group consisting of α- or β-tricalciun phosphate, hydroxyapatite, calcium sulfate hemi-hydrate, calcium carbonate, and the mixture thereof. Hydroxyapatite's chemical formula is $Ca_{10}(PO_4)_6(OH)_2$, its components and crystalline structure is similar to those of bioapatite; it has good biocompatibility, binds bone tissue directly, has osteoconduction and induces bone regeneration. Tricalcium phosphate's chemical formula is $Ca_3(PO_4)_2$, its biocompatibility is similar to that of hydroxapatite; it binds bone tissue directly and has good bioresorbability. The chemical formula of calcium sulfate hemi-hydrate is $CaSO_4 \cdot 1/2H_2O$, it mixes with water to form $CaSO_4 \cdot 2H_2O$, and it is bioresorbable. The chemical formula of calcium carbonate is $CaCO_3$, it has good bioresorbability and can be absorbed by tissues in several months to 1 year as it is implanted. The diameter length of bioceramic particle affects the interaction between tissue and bioceramic material, if the bioceramic particle is too big which can not be absorbed by living tissues and there is fiber induced around the particle. When the particle diameter is less than 5 μm, the particle can be digested by macrophage. The microsphere composite of this invention comprises about 1–99% of bioceramic powder by weight with respect to the total weight of the microsphere composite, and the diameter of the bioceramic powder is about less than 5 μm.

Alginate is a natural polysaccharide polymer and non-toxic, and it dissolves in water or basic solution to form viscous solution but does not dissolve in organic solvent or acid solution. It is negatively charged polymer under physiological solution enviromnent, and binds many kinds of divalent cations to form gels. Thus, it is applied to coat cells and drugs. Alginate is prepared as about 0.1–10 w/v % for use in this invention.

This invention uses a vessel having a needle or connecting with a needle and an air jet-syringe pump extrusion (e.g., an syringe pump), to squeeze the mixture solution of collagen solution, bioceramic powder and alginate into spherical droplet. That is, first transfer the mixture solution to the vessel, then load an air jet-syringe pump extrusion with the vessel, finally operate the air jet-syringe pump extrusion. Thus the mixture solution is squeezed into spherical droplets being discharged at the outlet of the needle into a divalent cation solution to undergo gelling to form microspheres. Gas source (e.g., a nitrogen gas tank) can be connected to a pipe installed in the air jet-syringe pump extrusion so that gas can be supplied to the outlet of the needle. The operation gas flowrate in the pipe can be regulated to control the size of the spherical droplet to obtain various sizes of microsphere when the air jet-syringe pump extrusion is operated. The larger the gas flowrate is, the smaller the microsphere diameter is. The gas used is selected from the group consisting of nitrogen gas, helium gas, argon gas, oxygen gas, carbon dioxide gas, and air, etc.

The cation of the divalent cation solution used in this invention is selected from the group consisting of $Cu^{2+}$, $Pb^{2+}$, $Ca^{2+}$, $Ba^{2+}$, $Cd^{2+}$, $Co^{2+}$, $Zn^{2+}$, $Mn^{2+}$, $Ni^{2+}$, and $Sr^{2+}$, etc. The mechanical strength of the gel formed by alginate and divalent cation increases with the increasing attractive force between alginate and divalent cation. Since human body contains calcium ion, calcium ions is used to undergo gelling. The divalent ion solution is prepared as about 0.1–10 w/v % for use in this invention.

Chitosan, poly (β-1,4-D-glucosarnine), is a crystalline polysaccharide, and its molecular structure is similar to that of cellulose. Chitosan has biocidal activity, good biocompatibility, and wide applications in biomedicine. In addition, the amino group of chitosan is positively charged as chitosan is in acidic environment. The present invention uses this characteristic to coat microspheres containing negative charged alginate with chitosan. Thus chitosan is used to maintain the shape of microsphere and provide it with enough mechanical strength to maintain its structure so that it can be used as a carrier. In the period of liquefying microsphere, wherein interior alginate is washed out and surface chitosan is washed away step by step at the same time. Chitosan is dissolved in acidic solution to form chitosan solution with pH of 4.5–6.5 which is the form of chitosan used in this invention, and the weight percentage of chitosan in the solution is about 0.00001%–10%. The acid in the acidic solution is selected from the group consisting of formic acid, acetic acid, propionic acid, lactic acid, malic acid, citric acid, ascorbic acid, oxalic acid, succinic acid, malonic acid, adipic acid, pyruvic acid, glutaric acid, tartaric acid, asparagic acid, epoxysuccinic acid, monochloroacetic acid, salicylic acid, itaconic acid, pyrrolidone carboxylic acid, glycolic acid, nitric acid, sulfuric acid, hydrochloric acid, phosphoric acid, and the mixture thereof.

This invention uses an aqueous buffer solution, such as phosphate based buffer, to liquefy and wash out interior alginate of microsphere and take surface chitosan of microsphere away, while collagen in the microsphere is reconstituted at about 35–40° C. to fibers network during this period. The phosphate based buffer is selected from the group consisting of phosphate buffer (PB), sodium citrate solution, and the mixture thereof and used to liquefy alginate gel in the microsphere. The rate of washing out the interior alginate and taking the surface chitosan away increases with increasing concentration of the phosphate based buffer. The required time of a complete wash out is controlled by the phosphate based buffer concentration. Therefore, collagen can have enough time to be reconstituted by controlling the level of phosphate based buffer concentration. This invention uses about 0.001–1 M phosphate buffer, and pH of which is in physiological range, about 7.2–7.4.

A scanning electron microscope is used to observe the interior structure and surface conformation of the microsphere composite prepared in accordance with the invention. Further, a light microscope is used to observe the distributions of collagen and bioceramic powder in the microsphere and the diameter length of the microsphere.

The present invention will be better understood from the following Examples which are merely for the purpose of illustration and by no means of any limitation therefore.

EXAMPLE 1

With reference to FIG. 1, carry out the following steps to prepare microsphere composites of collagen and bioceramic powder:

1. Take 6 ml of 6 mg/ml purified atelopeptides of type I collagen solution, 66.86 mg of β-tricalcium phosphate powder, 1.8 ml of 6% alginate (KELTONE® HV, Kelco Corporation), and 1.2 ml of phosphate buffer saline (PBS). Agitate the mixture solution well to have perfect mixing of the components. The ratio of collagen to β-tricalcium phosphate (w/w) in the mixture solution is 35:65.
2. Transfer the mixture solution prepared in step 1 to a vessel, load a RAZELT™ syringe pump (model A-99, Razel Scientific Instruments, Inc.) with the vessel connecting a needle and operate the syringe pump system (a pipe is installed in the syringe pump so that gas can be supplied to the outlet of the needle via this pipe and a gas source) to squeeze the mixture solution in the vessel to spherical droplets, which are discharged into 1.5% calcium chloride solution (a divalent cation solution) to undergo gelling to form microsphere. The operation gas flowrate of the syringe pump system is 5 ml/min nitrogen gas. The operation temperature of this step is about 4° C. to prevent reconstitution of collagen.
3. Replace the calcium chloride solution of step 2 with Ca-CHES (2-N-cyclohexylaminoethane-sulfuric acid), and immerse the microsphere prepared in step 2 in Ca-CHES at 4° C. for 5 minutes. Again, replace the Ca-CHES solution with 0.05 w/v % chitosan solution (pH 5.5), which is prepared by dissolving chitosan in 0.05% lactic acid solution, and coat the microsphere with the chitosan solution for 5 minutes. Then, use 0.5 M phosphate buffer to liquefy the interior and surface of the microsphere for 5 minutes to wash out the interior alginate and the surface chitosan partially. The above operations are carried out at room temperature.
4. Use 0.02 M phosphate buffer to liquefy the microsphere obtained in step 3 at about 37° C., and at various time intervals, 1, 3, 6, 9, 12, 24 hours after the initial wash, immerse the microsphere in fresh phosphate buffer in order to wash out interior alginate and surface chitosan of the microsphere completely, while collagen in the microsphere is reconstituted to fibers network at the same time.
5. Use phosphate buffer saline to wash the microsphere obtained in step 4, and such washed collagen microspheres containing bioceramic powder are freeze-dried and preserved at about −20° C. or directly preserved in phosphate buffer saline at about 4° C.

Figure 2B:
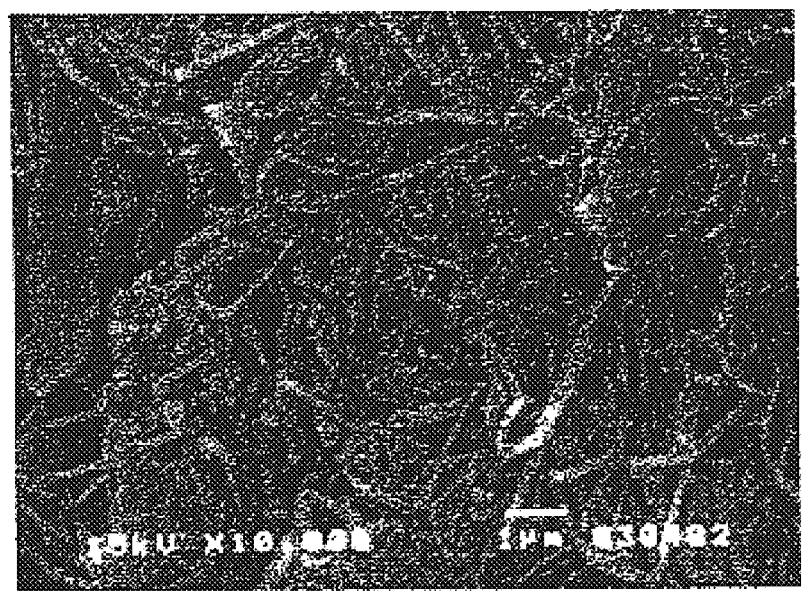
FIG. 2B shows a SEM micrograph of the surface of the microsphere composite after the 9 hours wash (Example 1), and the magnification is 10000×.
Figure 2C:
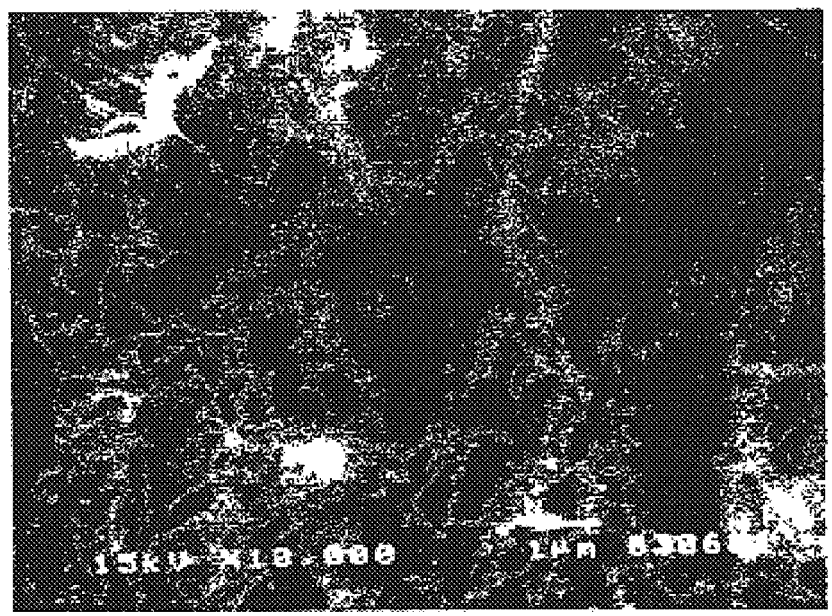
FIG. 2C shows a SEM micrograph of the cross section of the microsphere composite after the 24 hours wash (Example 1), and the magnification is 10000×.
Figure 2D:
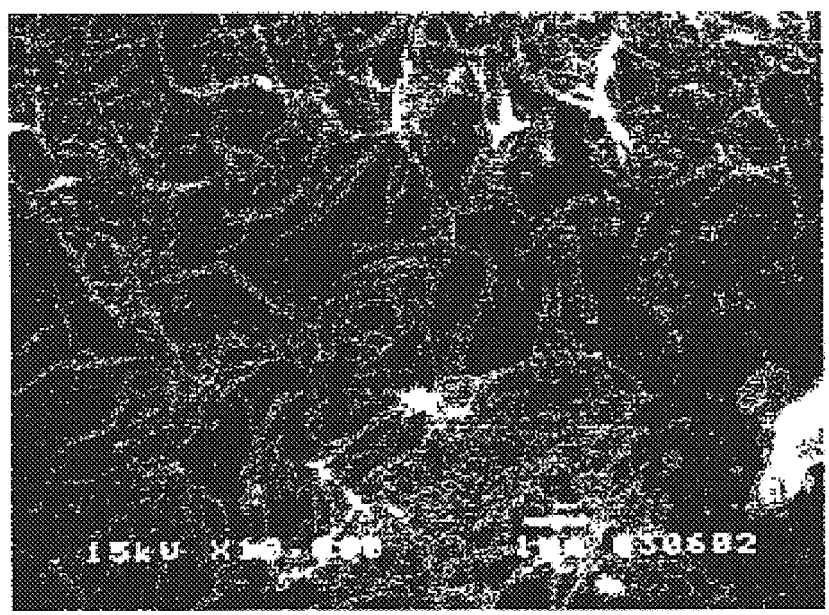
FIG. 2D shows a SEM micrograph of the surface of the microsphere composite after the 24 hours wash (Example 1), and the magnification is 10000×.

A light microscope is used to observe the microsphere composite prepared in this example, the observations show that collagen and β-tricalcium phosphate are distributed homogeneously in the microsphere. As described in step 4, fresh phosphate buffer is used at different time intervals to wash out interior alginate of the microsphere, therefore, we can understand if all the alginate is washed out by assaying alginate content in the phosphate buffer used at each time interval. The experimental results show that about 90% and about 100% of the alginate is washed out by the 9 hours and 12 hours wash respectively. In addition, the cross section and surface of the microsphere at different time intervals are observed by a scanning electron microscope, and the SEM micrographs are shown in FIG. 2A to FIG. 2D. FIG. 2A and FIG. 2B show a SEM micrograph of the cross section and surface of the microsphere composite after the 9 hours wash respectively, and FIG. 2C and FIG. 2D show those after the 24 hours wash respectively. The magnification of all the SEM micrographs is 10000×. These SEM micrographs show that, with respect to the microsphere after the 9 hours wash, the interior and the surface of the microsphere have collagen fiber network, and there is some residual chitosan on the microsphere surface; with respect to the microsphere after the 24 hours wash, the interior and the surface of the microsphere have collagen fiber network, and most of the chitosan are washed away from the microsphere surface. The average diameter of the microsphere composite prepared in this Example is 1560±70 µm.

EXAMPLE 2

Follow the same operations of all the steps of Example 1, except 0.005 w/v % chitosan solution (pH 5.5), instead of 0.05 w/v % chitosan solution, is used to coat the microsphere for five minutes in step 3. The 0.005 w/v % chitosan solution is prepared by dissolving chitosan in 0.005% lactic acid.

Figure 3A:
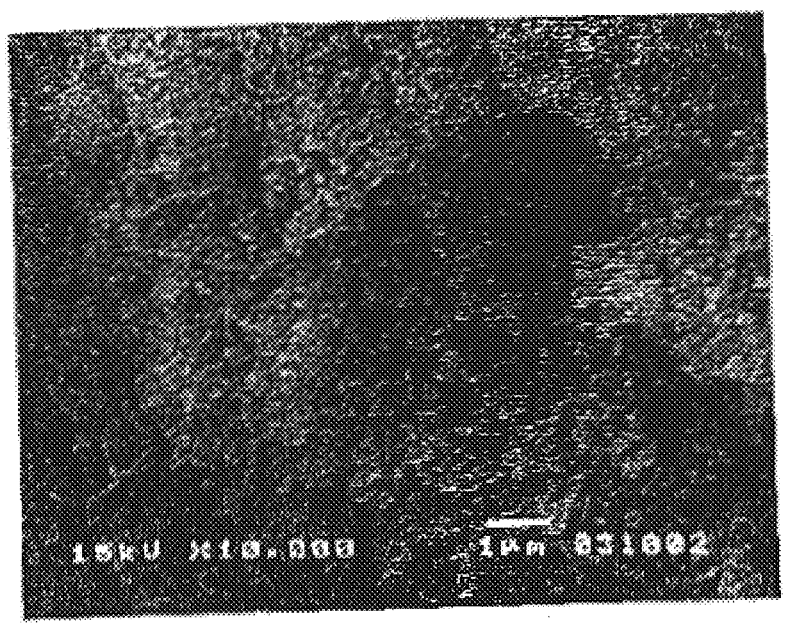
FIG. 3A shows a SEM micrograph of the cross section of the microsphere composite after the 9 hours wash (Example 2), and the magnification is 10000×.
Figure 3B:
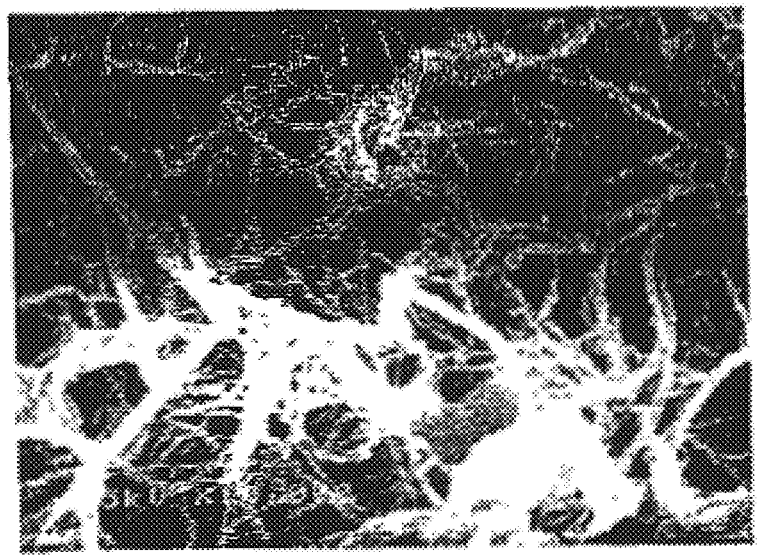
FIG. 3B shows a SEM micrograph of the surface of the microsphere composite after the 9 hours wash (Example 2), and the magnification is 10000×.
Figure 3C:
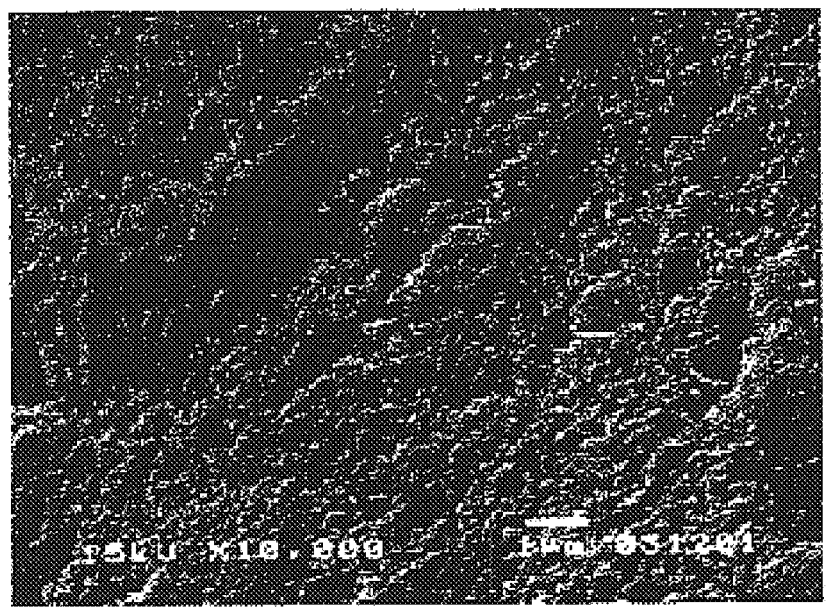
FIG. 3C shows a SEM micrograph of the cross section of the microsphere composite after the 24 hours wash (Example 2), and the magnification is 10000×.
Figure 3D:
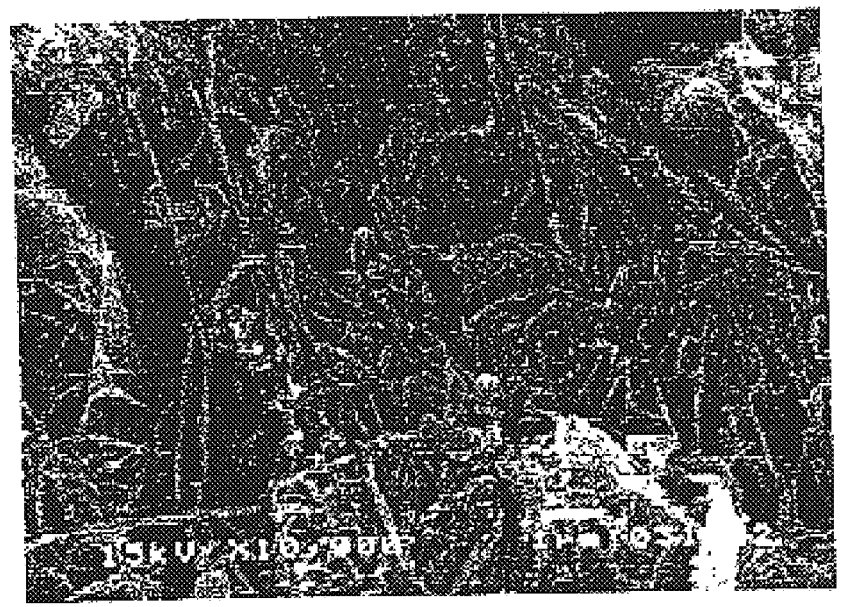
FIG. 3D shows a SEM micrograph of the surface of the microsphere composite after the 24 hours wash (Example 2), and the magnification is 10000×.

The experimental results show that about more than 95% and about 100% of alginate in the microsphere is washed out after the 9 hours and 12 hours wash respectively. In addition, the cross section and surface of the microsphere at different time intervals are observed by a scanning electron microscope, and the SEM micrographs are shown in FIG. 3A to FIG. 3D. FIG. 3A and FIG. 3B show a SEM micrograph of the cross section and the surface of the microsphere composite after the 9 hours wash respectively, and FIG. 3C and FIG. 3D show those after the 24 hours wash respectively. The magnification of all the SEM micrographs is 10000x. These SEM micrographs show that, with respect to the microsphere after the 9 hours wash, the interior and the surface of the microsphere have collagen fiber network structure, and there is residual chitosan on the surface; with respect to the microsphere after 24 hours wash, the interior and the surface of the microsphere have collagen fiber structure, and almost all the surface chitosan are washed away from the microsphere surface with the washed out alginate.

EXAMPLE 3

Follow the same operations of all the steps of Example 1, except in step 1 take the quantities of collagen solution and β-tricalcium phosphate to prepare the mixture solution such that the ratio of collagen to β-tricalcium phosphate (w/w) is 25:75, instead of 35:65. The SEM micrographs for the microsphere composite of this Example are similar to those of Examples 1, 2, therefore the interior and the surface of the microsphere have collagen fiber network structure. The higher the collagen content in the microsphere composite is, the higher the degree of fiber network structure is, the weaker the mechanical strength of the microsphere is, and the higher the preparation cost is; while the lower the collagen content is, the lower the preparation cost is, the weaker the mechanical strength of the microsphere is, and the lower the degree of fiber network structure is; therefore, collagen structure in the microsphere is not similar to collagen fiber network structure in bone tissue, and osteoblast cells can not grow in the microsphere. Generally speaking, the ratio of collagen to bioceramic powder (w/w) is in the range of about 10:90 to 90:10, and the ratio of 35:65 is the best since which is similar to the ratio value corresponding to bone tissue.

EXAMPLE 4

Follow the same operations of all the steps of Example 1, except in step 2 the nitrogen gas flowrate of the syringe pump system is 7.5 ml/min, instead of 5 ml/min. The SEM micrographs for the microsphere composite of this Example are similar to those of Example 1, therefore the interior and the surface of the microsphere have collagen fiber network structure and the average diameter of the microsphere is 835±36 μm.

EXAMPLE 5

Follow the same operations of all the steps of Example 1, except in step 1 the nitrogen gas flowrate of the syringe pump system is 10 ml/min, instead of 5 ml/min. The SEM micrographs for the microsphere composite of this Example are similar to those of Example 1, therefore the interior and the surface of the microsphere have collagen fiber network structure and the average diameter of the microsphere is 210±12 μm. The operation gas flowrate of the syringe pump system can be regulated to get different sizes of microsphere; the larger the gas flowrate is, the smaller the diameter of the microsphere is.

EXAMPLE 6

Follow the same operations of all the steps of Example 1, except in step 1 hydroxyapatite powder is used to replace β-tricalcium phosphate powder. The SEM micrographs for the microsphere composite of this Example are similar to those of Examples 1, therefore the interior and the surface of the microsphere have collagen fiber network structure. The light microscopy observations for the microsphere composite are similar to those of Example 1 too. Therefore, the bioceramic powder material used in this invention can be selected from the group consisting of α- or β-tricalcium phosphate, hydroxyapatite, calcium sulfate hemi-hydrate, calcium carbonate, and the mixture thereof.

EXAMPLE 7

Follow the same operations of all the steps of Example 1, except 6 ml of 6 mg/ml purified atelopeptides of type II collagen solution is used to replace purified atelopeptides of type I collagen solution in step 1. The SEM micrographs and light microscopy micrographs for the microsphere composite prepared accordingly are similar to those of Examples 1, therefore the interior and the surface of the microsphere have collagen fiber network structure. In addition, the bioceramic powder material used in this Example can be selected from the group consisting of α- or β-tricalcium phosphate, hydroxyapatite, calcium sulfate hemi-hydrate, calcium carbonate, and the mixture thereof.

The diameter of the microsphere composite prepared in accordance with this invention can be in the range of about 50 μm–5 mm, and the microsphere composite and the method of preparing the same have the following advantages:

1. As purified atelopeptides of collagen is used to prepare the microsphere composite, degree of immune response caused by it is low as it is applied to tissue;
2. The preparation of the microsphere composite is carried out in aqueous solution systems, i.e., no organic solvent or organic oil is involved. Therefore, there is no damage to collagen caused by organic solvents, and no need to worry about tissue damage caused by residual organic oil as the microsphere composite is applied to tissue;
3. The microsphere composite has enough mechanical strength to maintain its shape and structure, and no cross linking agent is used to cross link collagen with bioceramic powder. Therefore, no tissue damage is caused by the cross linking agent as the microsphere composite is applied to tissue;
4. The microsphere interior and surface have collagen fibers network due to the reconstitution of collagen during the period of the preparation;
5. Bioceramic powder is distributed homogeneously in the collagen fiber network;
6. Different sizes of the microsphere composite is obtained based on different operation conditions of squeezing the mixture solution of collagen, bioceramic powder and alginate to spherical droplets, e.g., on the operation gas flowrate as an air jet-syringe pump extrution is used to squeeze the mixture solution;
7. The microsphere composite has enough mechanical strength to be used as a carrier to carry cells, coat and fix different bone growth factors to induce tissue regeneration and speed up bone repair rate;
8. The reaction conditions of preparing the microsphere composite are gentle and do not cause damages to cells, therefore the microsphere prepared is suitable for coating cells or tissues. It can be prepared in injectable forms or different shapes of plate to be applied to repair human tissues;

9. The materials used to prepare the microsphere composite such as collagen, bioceramic powder, alginate, and chitosan have been approved by Food and Drug Administration (FDA) for use in human;

10. The microsphere composite has similar composition components of bone tissues and collagen fiber network structure, so it can provide the similar cell culturing environment of bone tissues and be applied to repair bone defect.

Although preferred embodiments have been described to illustrate the present invention, it is apparent that changes and modifications in the described embodiments can be carried out without departing from the scope of the invention intended to be limited only by the appended claims.

What is claimed is:

1. A method of preparing microsphere composite of collagen and bioceramic powder, comprising the steps of:

mixing a collagen solution with bioceramic powder and alginate to form a mixture solution;

squeezing the mixture solution to spherical droplet being discharged into a divalent cation solution undergoing gelling to produce microsphere;

coating the microsphere with a chitosan solution to support the shape of the microsphere; and liquefying and washing out interior alginate and surface chitosan of the microsphere with an aqueous buffer solution, while collagen in the microsphere is reconstituted to fiber network at the same time to obtain microsphere composite.

2. The method as claimed in claim 1, wherein the microsphere composite contains about 1–99% collagen by weight with respect to the total weight of the microsphere composite.

3. The method as claimed in claim 1, wherein the collagen solution is at a concentration of about 0.1–20 mg/ml.

4. The method as claimed in claim 1, wherein the bioceramic powder is selected from the group consisting of α- or β-tricalcium phosphate, hydroxyapatite, calcium sulfate hemi-hydrate, calcium carbonate, and the mixture thereof.

5. The method as claimed in claim 1, wherein the microsphere composite contains about 1–99% bioceramic powder by weight with respect to the total weight of the microsphere composite.

6. The method as claimed in claim 1, wherein the diameter of the bioceramic powder is about less than or equal to 5 $\mu$m.

7. The method as claimed in claim 1, wherein the mixture solution contains about 0.1–10 w/v % alginate.

8. The method as claimed in claim 1, wherein the mixing step comprises the step of agitating the mixture solution well.

9. The method as claimed in claim 1, wherein the mixing step is carried out at about 0–10° C.

10. The method as claimed in claim 1, wherein the squeezing step comprises the steps of transferring the mixture solution to a vessel having a needle or connecting with a needle, loading an air jet-syringe pump extrusion with the vessel, and operating the air jet-syringe pump extrusion to squeeze the mixture solution into spherical droplet.

11. The method as claimed in claim 1, wherein the divalent cation solution comprises an cation which is selected from group consisting of $Cu^{2+}$, $Pb^{2+}$, $Ca^{2+}$, $Ba^{2+}$, $Cd^{2+}$, $Co^{2+}$, $Zn^{2+}$, $Mn^{2+}$, $Ni^{2+}$, and $Sr^{2+}$.

12. The method as claimed in claim 1, wherein the divalent cation solution is at a concentration of about 0.1–10 w/v %.

13. The method as claimed in claim 1, wherein the chitosan solution is formed by dissolving chitosan in an acid solution, and the weight percentage of chitosan in the chitosan solution is about 0.00001%–10%.

14. The method as claimed in claim 1, wherein the chitosan solution is formed by dissolving chitosan in an acid solution and the weight percentage of chitosan in the chitosan solution is about 0.00001%–10%, said acid solution comprises an acid selected from the group consisting of formic acid, acetic acid, propionic acid, lactic acid, malic acid, citric acid, ascorbic acid, oxalic acid, succinic acid, malonic acid, adipic acid, pyruvic acid, glutaric acid, tartaric acid, asparagic acid, epoxysuccinic acid, monochloroacetic acid, salicylic acid, itaconic acid, pyrrolidone carboxylic acid, glycolic, acid, nitric acid, sulfuric acid, hydrochloric acid, phosphoric acid, and the mixture thereof.

15. The method as claimed in claim 1, wherein the aqueous buffer solution is selected from the group consisting of phosphate buffer solution, sodium citrate solution, and the mixture thereof.

16. The method as claimed in claim 15, wherein the phosphate buffer solution is at a concentration of about 0.001–1 M.

17. The method as claimed in claim 1, wherein the diameter of the microsphere composite is in the range of about 50 $\mu$m–5 mm.

18. The method as claimed in claim 1, wherein the liquefying is carried out at about 35–40° C.

* * * * *